United States Patent [19]

Schröer

[11] Patent Number: 5,808,014

[45] Date of Patent: Sep. 15, 1998

[54] PROCESS FOR THE PREPARATION OF ARLAZOTETRONIC ACID DERIVATIVES

[75] Inventor: Josef Schröer, Naters, Switzerland

[73] Assignee: Lonza, AG, Gampel/Valais, Switzerland

[21] Appl. No.: 922,602

[22] Filed: Sep. 3, 1997

[30] Foreign Application Priority Data

Sep. 4, 1996 [CH] Switzerland .............................. 2178/96

[51] Int. Cl.$^6$ .................................................. C07D 307/33
[52] U.S. Cl. ............................ 534/582; 534/753; 549/313
[58] Field of Search ....................... 534/582, 753

[56] References Cited

U.S. PATENT DOCUMENTS

| | | | |
|---|---|---|---|
| 2,226,198 | 12/1940 | Dickey et al. | 534/753 |
| 4,851,540 | 7/1989 | McGarrity et al. | 548/110 |
| 5,162,540 | 11/1992 | McGarrity et al. | 548/303.1 |
| 5,298,658 | 3/1994 | Fabricius | 564/251 |

OTHER PUBLICATIONS

Tanaka et al., Chem. Pharm. Bull., 32(8), 3291–3298, (1984).

Meul et al., Chemical Abstracts, 108:55 786 (1988).

*Primary Examiner*—Fiona T. Powers
*Attorney, Agent, or Firm*—Fisher, Christen & Sabol

[57] ABSTRACT

A process for the preparation of arylazotetronic acid derivatives of the general formula:

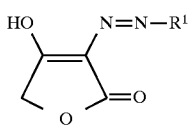

in which a 3-chloro-4-hydroxy-2(5H)-furanone of the formula:

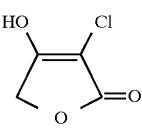

is diazotized. The arylazotetronic acid derivatives are important intermediates in the preparation of (+)-biotin.

4 Claims, No Drawings

PROCESS FOR THE PREPARATION OF ARLAZOTETRONIC ACID DERIVATIVES

BACKGROUND OF THE INVENTION

1. Field Of The Invention

The invention relates to a novel process for the preparation of arylazotetronic acid derivatives of the general formula:

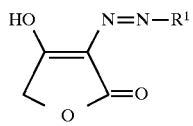

wherein $R^1$ is an optionally substituted phenyl group.

2. Background Art

Arylazotetronic acid derivatives are important intermediates in the preparation of (+)-biotin. (+)-Biotin, which is also known as vitamin H, is used, inter alia, for pharmaceutical applications and also as an additive in animal feeds. Numerous syntheses for the preparation of (+)-biotin have been published. For example, the total synthesis of (+)-biotin starting from tetronic acid published in European Published Patent Aplication No. 0270076 and in European Published Patent Application No. 0273270 have gained commercial significance. The tetronic acid used as starting material in this total synthesis was prepared according to European Published Patent Application No. 0153615 starting from a 4-chloroacetoacetic ester by chlorination with sulfuryl chloride to give the 2,4-dichloroacetoacetic ester, thermal treatment and ring closure to give the 3-chlorotetronic acid and, finally, hydrogenation of the chlorotetronic acid. Only then could the diazotization be carried out in a further, fourth step according to the cited European Published Patent Application No. 0270076. It is clear that the above preparation of the starting materials is complex.

BROAD DESCRIPTION OF THE INVENTION

The main object of the invention is to develop and provide a process which does not have the above-stated disadvantage. Other objects and advantages of the invention are set out herein or are obvious herefrom to one skilled in the art.

The objects and advantages of the invention are achieved by the process of the invention.

The invention includes a process for the preparation of an arylazotetronic acid derivative of the general formula:

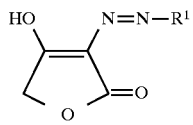

wherein $R^1$ is an optionally substituted phenyl group. According to the process of the invention, 3-chloro-4-hydroxy-2(5H)-furanone of the formula:

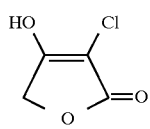

is reacted with a diazonium salt of the general formula:

wherein $R^1$ is as defined above, and X is an acid anion.

DETAILED DESCRIPTION OF THE INVENTION

3-Chloro-4-hydroxy-2(5H)-furanone can be prepared as described above according to European Published Patent Application No. 0153615 from the 4-chloroacetoacetic ester.

The diazonium salt is prepared by a long-known method (cf. European Published Patent Application No. 0270076) by reacting a corresponding aniline with an aqueous mineral acid in the presence of an alkali metal nitrite.

$R^1$ is preferably a phenyl group. Examples of substituents for the phenyl group are: $C_{1-6}$-alkyl, i.e., expediently methyl, ethyl, n-propyl, isopropyl, n-butyl, sec-butyl, tert-butyl, pentyl or hexyl or its isomers, $C_{1-6}$-alkoxy, aryl, i.e., expediently phenyl, or aryloxy, such as, phenoxy.

X as an acid anion is expediently an anion of a mineral acid, i.e., a halogen atom, for example, fluorine, chlorine, bromine or iodine, or hydrogen-sulfate or $BF_4$.

The preferred diazonium salt is the benzene-diazonium chloride prepared from aniline and hydrochloric acid wherein $R^1$ is phenyl and X is chlorine.

The diazonium salt is advantageously added to an aqueous solution of 3-chloro-4-hydroxy-2(5H)-fluronone which has been adjusted to a pH of from 2 to 7 and which expediently has a temperature of from −20° to 20° C. The diazotization is preferably carried out at a temperature of from −10° to 10° C.

The resultant arylazotetronic acid derivative usually precipitates out and can, thus, easily be isolated from the reaction mixture in very good yield and purity.

EXAMPLE 1.4 ml of aniline (15.4 mmol) followed by a solution of 1.0556 g of sodium nitrite (15.3 mmol) in 3 ml of water were added dropwise at −10° C. to 7 ml of a semi-concentrated aqueous hydrochloric acid (about 16 percent). After 10 minutes a pale yellow, clear solution was titrated at the same temperature with a saturated solution of aqueous sodium acetate until a color change to deep yellow was observed. At the same time the solution became cloudy. A suspension of 3-chloro-4-hydroxy-2(5H)-furanone in 20 ml of water was adjusted to about pH 6 using 1 M aqueous sodium hydroxide solution, giving a clear solution. This solution was cooled to −10° C. The diazonium salt reagent prepared previously was then added dropwise. A thick yellow-orange precipitate was formed during this operation. The cooling bath was removed, and the mixture was allowed to warm to room temperature. 2.4 g of sodium thiosulfate (15.2 mmol) was added as a solid, and the mixture was stirred for 5 minutes and filtered. The precipitate was washed with 50 ml of water. The deposition of further product was observed in the filtrate and was also recovered by filtration. Both product fractions were dried in a vacuum at 50° C. for 18 hours. A total of 1.2232 g of 3-phenylazotetronic acid was obtained. The yield of the product was 39 percent. Other data concerning the product was:

$^1$H—NMR (CDCl$_3$, 400 MHz)δ:4.50 (d, 2H); 7.36 (m, 1H); 7.48 (m, 2H); 7.58 (m, 2H); 13.12 (br,s 0.5H); 14.00 (br,s 0.5H).

What is claimed is:

1. A process for the preparation of an arylazotetronic acid derivative of the formula:

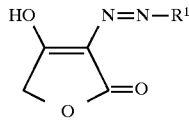   I wherein $R^1$ is an optionally substituted phenyl group, comprising converting 3-chloro-4-hydroxy-2(5H)-furanone of the formula:

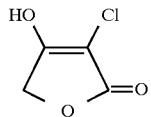   II using a diazonium salt of the formula:

   III wherein $R^1$ is defined as above, and X is an acid anion, into the arylazotetronic acid derivative of formula I.

2. The process according to claim 1, wherein the diazotization is carried out at a temperature of from −20° to 20° C.

3. The process according to claim 2, wherein the diazonium salt is added to an aqueous solution of 3-chloro-4-hydroxy-2(5H)-furanone which has been adjusted to a pH of from 2 to 7.

4. The process according to claim 1, wherein the diazonium salt is added to an aqueous solution of 3-chloro-4-hydroxy-2(5H)-furanone which has been adjusted to a pH of from 2 to 7.

\* \* \* \* \*